US006957957B2

(12) United States Patent
Pospisil (10) Patent No.: US 6,957,957 B2
(45) Date of Patent: Oct. 25, 2005

(54) MOLAR APPLIANCE FOR ORTHODONTIC THERAPY

(75) Inventor: Jirina V. Pospisil, Hacienda Heights, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 136 days.

(21) Appl. No.: 10/287,165

(22) Filed: Nov. 4, 2002

(65) Prior Publication Data

US 2004/0086826 A1    May 6, 2004

(51) Int. Cl.[7] .................................................. A61C 3/00
(52) U.S. Cl. ................................. 433/11; 433/8; 433/10
(58) Field of Search .................................. 433/11, 8, 10

(56) References Cited

U.S. PATENT DOCUMENTS

| | | |
|---|---|---|
| 2,368,851 A | 2/1945 | Laskin |
| 3,578,744 A | 5/1971 | Wildman et al. |
| 3,772,787 A | 11/1973 | Hanson |
| RE28,889 E | 7/1976 | Wildman |
| 3,969,821 A | 7/1976 | Lee, Jr. et al. |
| 4,103,423 A | 8/1978 | Kessel |
| 4,149,314 A | 4/1979 | Nonnenmann |
| 4,248,588 A | 2/1981 | Hanson |
| 4,260,375 A | 4/1981 | Wallshein |
| 4,371,337 A | 2/1983 | Pletcher |
| 4,492,573 A | 1/1985 | Hanson |
| 4,511,331 A | 4/1985 | Scebold et al. |
| 4,559,012 A | 12/1985 | Pletcher |
| 4,712,999 A | 12/1987 | Rosenberg |
| 4,725,229 A | 2/1988 | Miller |
| 4,820,151 A | 4/1989 | Pospisil |
| 4,878,840 A | 11/1989 | Reynolds |
| 4,927,362 A | 5/1990 | Snead |
| 5,059,119 A | 10/1991 | Snead |
| 5,094,614 A | 3/1992 | Wildman |
| 5,095,602 A | 3/1992 | Reher et al. |
| 5,151,028 A | 9/1992 | Snead |
| 5,230,620 A | 7/1993 | Watanabe |
| 5,269,681 A | 12/1993 | Degnan |
| 5,275,557 A | 1/1994 | Damon |
| 5,322,435 A | 6/1994 | Pletcher |
| 5,356,289 A | 10/1994 | Watanabe |
| 5,516,284 A | 5/1996 | Wildman |
| 5,613,850 A | 3/1997 | Wildman et al. |
| 5,685,711 A | 11/1997 | Hanson |
| 5,711,666 A | 1/1998 | Hanson |
| 5,913,680 A | 6/1999 | Voudouris |
| 6,247,923 B1 | 6/2001 | Vashi |
| 6,554,612 B2 * | 4/2003 | Georgakis et al. ............ 433/11 |

(Continued)

FOREIGN PATENT DOCUMENTS

EP          0 820 735         1/1998

(Continued)

*Primary Examiner*—Cary E. O'Connor
*Assistant Examiner*—Candice C. Stokes
(74) *Attorney, Agent, or Firm*—James D. Christoff (57) ABSTRACT

An orthodontic appliance for a molar tooth has a latch that is movable between an open position to admit or release an archwire into an archwire slot and a closed position to retain the archwire in the archwire slot. In one aspect of the invention, the appliance lacks tiewings and has a mesial archwire guide that is spaced from a distal archwire guide by a channel that extends in a generally occlusal-gingival direction across the appliance. In another aspect of the invention, the appliance includes a flange with at least one groove for retaining a wire segment or other item in place.

15 Claims, 5 Drawing Sheets

U.S. PATENT DOCUMENTS

| | | |
|---|---|---|
| 6,709,268 B2 | 3/2004 | Pospisil et al. |
| 6,733,285 B2 | 5/2004 | Puttler et al. |
| 2001/0029008 A1 | 10/2001 | Jordan et al. |
| 2004/0086825 A1 | 5/2004 | Lal et al. |

FOREIGN PATENT DOCUMENTS

| | | |
|---|---|---|
| WO | WO 01/22901 | 4/2001 |
| WO | WO 02/089693 | 11/2002 |

* cited by examiner

MOLAR APPLIANCE FOR ORTHODONTIC THERAPY

BACKGROUND OF THE INVENTION

1. Field of the Invention

This invention broadly relates to appliances that are used during the course of orthodontic treatment. More particularly, the present invention relates to an orthodontic appliance that is affixed to one of the patient's molar teeth.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into an archwire slot of each bracket. The archwire forms a track to guide movement of the teeth to orthodontically correct locations.

End sections of orthodontic archwires are typically captured in tiny appliances known as buccal tubes. Buccal tubes are affixed to the patient's molar teeth. In the past, buccal tubes were typically welded to bands having a configuration adapted to encircle the selected molar tooth. Recently, buccal tubes have become available that are adapted to be directly bonded to the surface of the patient's tooth by an adhesive.

Ligatures are often used in conjunction with orthodontic brackets to connect the archwire to the brackets and urge the archwire into an orientation of seating engagement in the archwire slot. One type of commercially available orthodontic ligature is a small, elastomeric O-ring. Orthodontic O-ring ligatures are installed by stretching the O-ring around small wings on the brackets that are known as tiewings. The tiewings are connected to the body of the bracket on its gingival side (i.e., the side facing the patient's gingiva or gums) and are also connected to the bracket body on its occlusal side (i.e., the side facing the outer tips of the patient's teeth). Once installed, the O-ring ligature extends around the back or lingual side of the tiewings as well as over the front or labial side of the archwire and urges the archwire toward a fully seated position in contact with a bottom or lingual wall of the archwire slot.

Metal ligatures, such as ligatures made of stainless steel, are also used to retain archwires in archwire slots of orthodontic brackets. Metal ligatures are typically made of a short section of initially straight wire that is subsequently formed into a loop. During installation, the wire ligature is hooked around the tiewings and extended over the labial side of the archwire. End sections of the archwire are then twisted together to close the loop and retain the ligature as well as the archwire in place.

Many types of orthodontic buccal tubes have an enclosed passageway for receiving the archwire, in contrast to the archwire slots of brackets that are open along one side. Some buccal tubes do not have tiewings since the enclosed passageway serves to capture the archwire. Buccal tubes are often of relatively simple construction, consisting essentially of a tubular body having a base that is adapted to be welded to an orthodontic band.

However, certain types of buccal tubes are known as "convertible" buccal tubes. These buccal tubes are often used on the first molar teeth of adolescent patients whose second molar teeth have not yet erupted. Convertible buccal tubes have an archwire passageway that is initially closed during the early stages of treatment. As treatment progresses and as the second molar tooth erupts, the passageway of the buccal tube on the first molar tooth is opened to convert the buccal tube into a bracket. Another buccal tube is then affixed to the patient's second molar teeth for capturing the ends of the archwire.

Examples of convertible buccal tube appliances are described in U.S. Pat. Nos. 4,511,331, 4,820,151, 4,927,362 and 5,059,119. Convertible buccal tubes often have a tab or cover that initially extends over and closes the archwire passageway. When it is desired to convert the buccal tube into a bracket, the tab or cover is opened to change the enclosed passageway into a slot that is open along one side. The practitioner then places a ligature around tiewings of the appliance and the archwire in order to retain the archwire in the archwire slot.

Unfortunately, some orthodontists are not entirely satisfied with elastomeric and metal ligatures used with orthodontic brackets and convertible buccal tubes. Such ligatures are somewhat time-consuming to install, both during initial installation and also during reinstallation whenever replacement of the archwire or ligatures is desired. As can be appreciated, decreasing the amount of time needed for ligation can help to reduce the total time that the practitioner must spend with the patient and consequently decrease the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed in the past having various types of latches for coupling the archwire to the bracket. Such brackets are also known as self-ligating or tieless brackets. The latch comprises a movable clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, the bracket illustrated in U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Improved self-ligating orthodontic brackets are described in two pending PCT applications entitled "ORTHODONTIC APPLIANCE WITH SELF-RELEASING LATCH", WO01/22901 and US02/09896. The appliances described in these applications have a latch for retaining an archwire in the archwire slot, and the latch releases the archwire from the archwire slot whenever the archwire exerts a force on the appliance that exceeds a certain minimum value. The minimum value is significantly less than the force required in the same direction to debond the appliance from the tooth, and consequently helps ensure that the appliance will not spontaneously debond from the tooth during the course of treatment.

In certain embodiments of the appliances described in the PCT applications mentioned above, the archwire may be inserted into the archwire slot by pressing the archwire against the latch. The latch is constructed to self-open without the need for hand instruments or other tools. Consequently, such appliances are a great advantage to the practitioner in that the time needed for connecting the archwire to the appliance can be significantly reduced.

The appliances described in the above-mentioned PCT applications include both brackets for the patient's anterior, cuspid and bicuspid teeth as well as appliances for the patient's molar teeth. While such appliances represent a significant advance in orthodontic appliance technology, there is a continuing need to improve the state of the art relating to self-ligating appliances. In particular, there is a need for an improved self-ligating appliance that is especially adapted for use with the patient's molar teeth. Preferably, any such appliance would provide a strong and secure coupling between the archwire and the associated molar tooth, and yet facilitate movement of the teeth when desired so that treatment can be completed without undue delay.

SUMMARY OF THE INVENTION

The present invention is directed toward improvements in self-ligating orthodontic appliances that are adapted for use with the molar teeth. In one aspect of the invention, the molar appliances have structure that affords good control over movement and positioning of the appliance when attaching the appliance to a tooth and also enable the practitioner to readily disengage the archwire from the appliance when desired. In another aspect of the invention, the molar appliances have structure that facilitates optional connection to other appliances or devices in the oral cavity, such as a tieback loop that is used to close spaces between adjacent teeth.

In more detail, the present invention in one embodiment relates to an orthodontic appliance for a molar tooth. The appliance includes a base for bonding the appliance to the surface of the molar tooth and a body extending from the base. The body has a mesial side portion and a distal side portion. A mesial archwire guide is connected to the mesial side portion of the body. A distal archwire guide is connected to the distal side portion of the body. An archwire slot extends across the mesial archwire guide and the distal archwire guide in a generally mesial-distal direction. The appliance also includes a latch for releasably retaining an archwire in the archwire slot. The latch is movable from a slot-open position for admitting the archwire in the archwire slot and to a slot-closed position for retaining the archwire in the archwire slot. The appliance lacks tiewings, and the mesial archwire guide is spaced from the distal archwire guide to present a channel that extends in a generally occlusal-gingival direction.

In another embodiment, the present invention is also directed to an orthodontic appliance for a molar tooth. In this embodiment, the appliance includes a base for bonding the appliance to a tooth and a body extending from the base. The body has a mesial side and a distal side. A mesial flange is located next to the mesial side of the body and a distal flange is located next to the distal side of the body. An archwire slot extends across the appliance in a generally mesial-distal direction. The appliance also includes a latch for releasably retaining an archwire in the archwire slot. The latch includes a mesial clip that is received between the mesial flange and the body, and a distal clip that is received between the distal flange and the body. At least one of the mesial flange and the distal flange has at least one groove adjacent the base for retaining a wire segment or other item in place.

Other aspects are described in the paragraphs that follow and are illustrated in the accompanying drawings.

DETAILED DESCRIPTION OF THE PREFERRED EMBODIMENTS

An orthodontic appliance for a molar tooth constructed according to one embodiment of the present invention is illustrated in FIGS. 1–6 and is broadly designated by the numeral 20. The appliance 20 includes a base 22 for bonding the appliance 20 directly to the patient's tooth enamel of a molar tooth by the use of an adhesive. Preferably, the base 22 has an outwardly-facing concave compound contour that matches the convex compound contour of the patient's molar tooth surface. Optionally, the base 22 may be provided with grooves, particles, recesses, undercuts, a chemical bond enhancement material or any other material or structure or any combination of the foregoing that facilitates bonding the appliance directly to the patient's tooth surface.

A body 24 is connected to the base 22 and extends outwardly from the base 22 in a generally buccolabial direction (i.e., a direction toward the patient's lips or cheeks). The body 24 optionally includes a notch 26 located along its occlusal and gingival sides. The notches 26 are useful as an aid for positioning the appliance 20 in a precise location on the base 22 during the manufacturing process. The appliance 20 also includes a mesial archwire guide 28 and a distal archwire guide 30. The mesial archwire guide 28 is integrally connected to a mesial side portion of the body 24 and the distal archwire guide 30 is integrally connected to a distal side portion of the body 24. Each of the archwire guides 28, 30 includes an occlusal arm and a gingival arm that extend in a buccolabial direction in a generally parallel relationship. The outermost buccolabial ends of the occlusal arm and the gingival arm have curved surfaces resembling a section of a cylinder.

Figure 1:
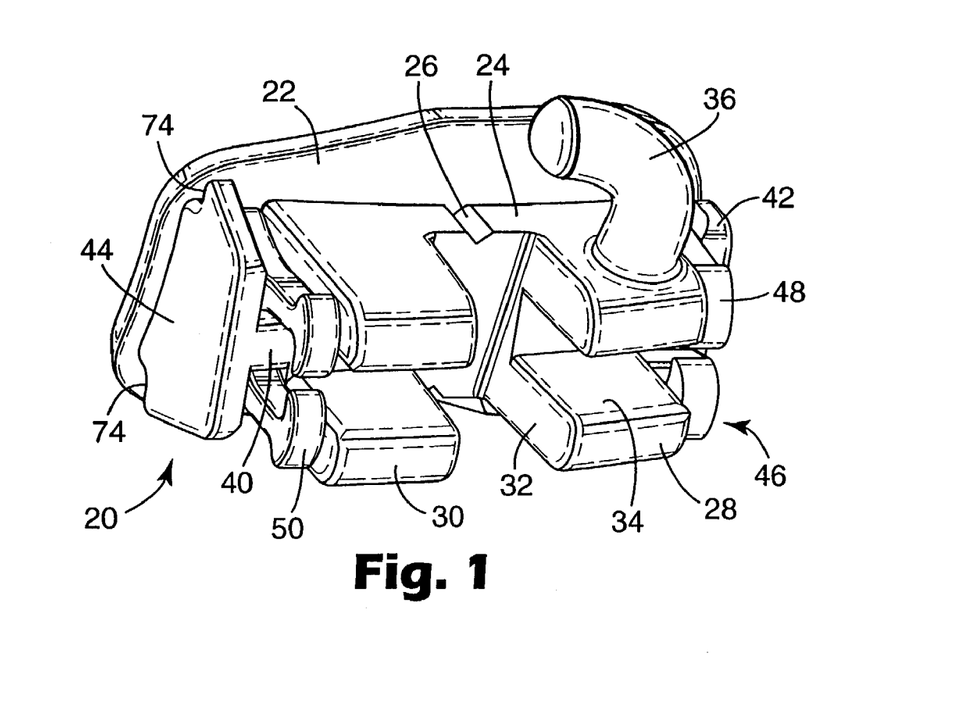
FIG. 1 is a perspective view of an exemplary orthodontic appliance constructed in accordance with the present invention, looking at the appliance toward its labial, distal and gingival sides.
Figure 2:
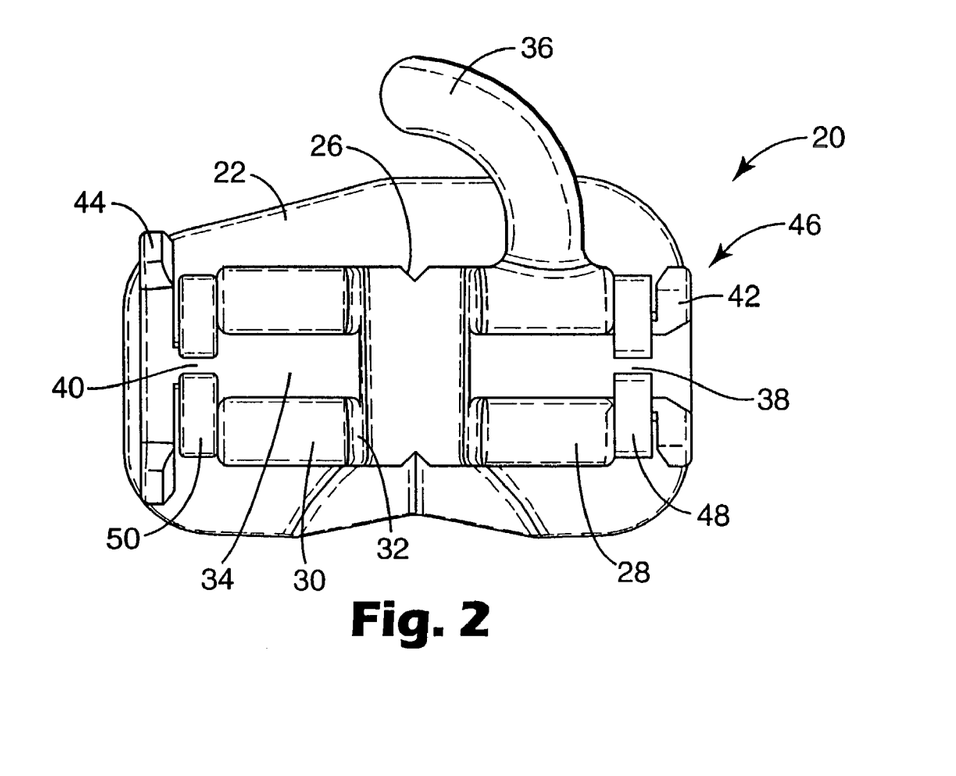
FIG. 2 is a front elevational view of the appliance depicted in FIG. 1, looking at the appliance toward its labial side.
Figure 3:
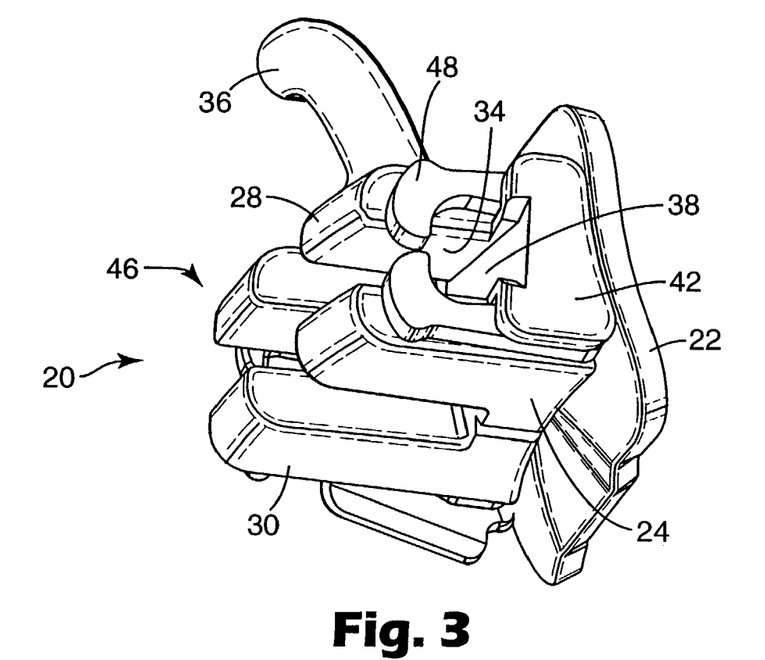
FIG. 3 is another perspective view of the appliance illustrated in FIGS. 1 and 2, looking at the appliance toward its mesial, occlusal and labial sides.
Figure 4:
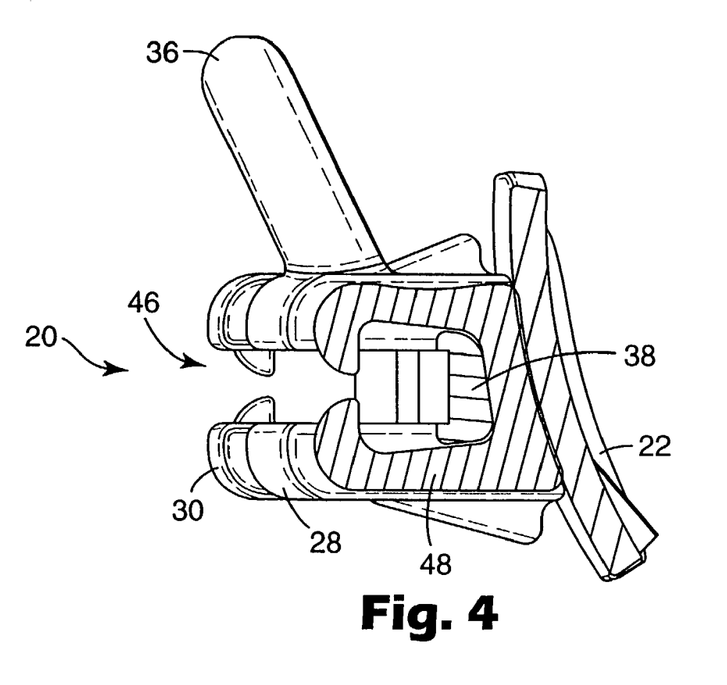
FIG. 4 is an end cross-sectional view of the appliance shown in FIGS. 1–3, looking at the appliance toward its mesial side.

The appliance 20 includes a channel 32 that extends in a generally occlusal-gingival direction. The channel 32 provides a space between the mesial archwire guide 28 and the distal archwire guide 30. A lingual side (i.e., the side facing the patient's tongue) of the channel 32 is directly adjacent and defined by an exposed buccolabial side of the body 24.

An elongated archwire slot 34 extends across the mesial archwire guide 28 and the distal archwire guide 30 in a generally mesial-distal direction. Preferably, the bottom or lingual side of the archwire slot 34 is spaced above the bottom of the channel 32 as shown for example in FIG. 1. The archwire slot 34 has occlusal and gingival sides that are defined by the occlusal and gingival arms respectively of the archwire guides 28, 30. The archwire slot 34 has a rectangular shape when viewed in a longitudinally transverse reference plane although a circular shape is also possible.

Optionally, and as shown in the illustrated embodiment, the appliance 20 includes a hook 36 that is integrally connected to the gingival arm of the mesial archwire guide 28. The hook 36 extends initially in a gingival direction from the mesial archwire guide 28 and then curves and extends in a distal direction. Preferably, the outer surfaces of the hook 36 are smooth in order to avoid irritating adjacent soft tissue of the patient.

A mesial support 38 is connected to the mesial archwire guide 28 and the mesial side of the body 24. In addition, a distal support 40 is connected to the distal archwire guide 30 and the distal side of the body 24. The mesial support 38 extends outwardly in a mesial direction and is coupled to a mesial flange 42. The distal support 40 extends outwardly in a distal direction and is coupled to a distal flange 44. A buccolabial side of the mesial and distal supports 38, 40 is coplanar with the bottom or lingual side of the archwire slot 34.

Figure 5:
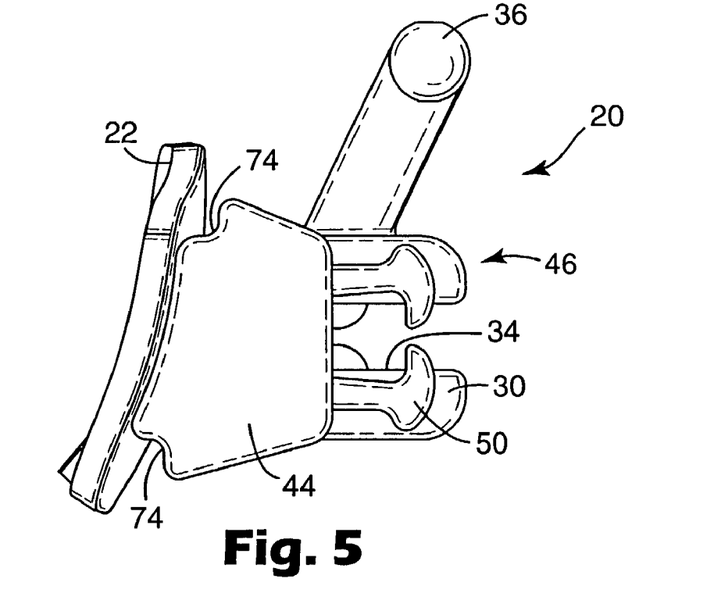
FIG. 5 is an end elevational view of the appliance shown in FIGS. 1–4, looking at the appliance toward its distal side.

As shown in FIGS. 1 and 5, the distal flange 44 increases in width in directions along an occlusal-gingival reference axis as the base 22 is approached. Preferably, the flanges 42, 44 are integral with the supports 38, 40 respectively. As another option, the flanges 42, 44 may be affixed to the supports 38, 40 after first being separately manufactured.

The appliance 20 also includes a latch 46 remote from the channel 32 for releasably retaining an archwire in the archwire slot 34. In the embodiment shown in the drawings, the latch 46 includes a mesial clip 48 located meisally of the mesial archwire guide and a distal clip 50 located distally of the distal archwire guide although other alternatives arc also possible. For example, the latch 46 could have only a single clip that is located in the channel 32. Other types of latches such as shutters, movable covers, spring members and the like may also be employed.

Figure 6:
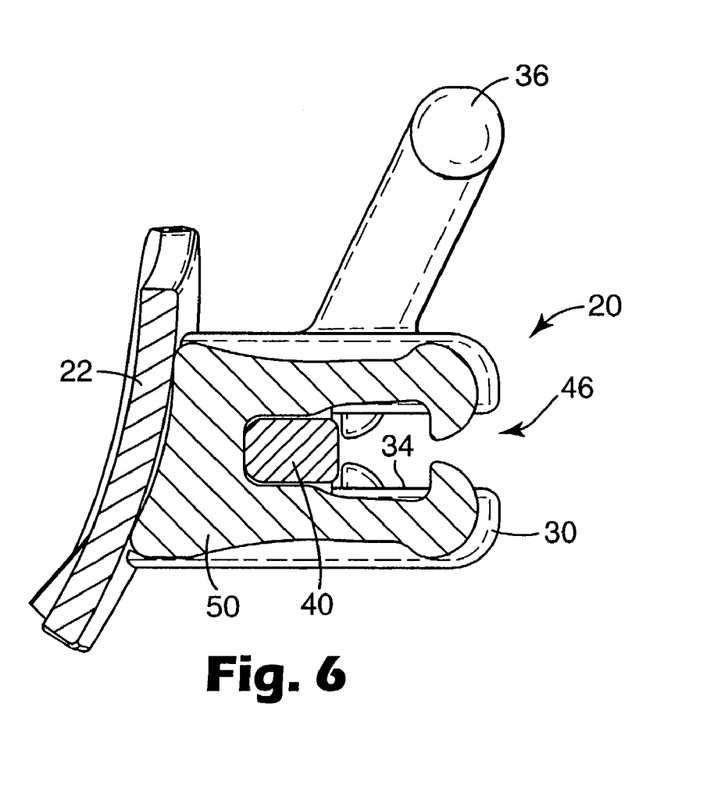
FIG. 6 is an enlarged end cross-sectional view of the appliance illustrated in FIGS. 1–5 and looking in the same direction toward the appliance as the view shown in FIG. 5.

The distal clip 50 is shown in the cross-sectional view of FIG. 6. As illustrated, the distal clip 50 has on overall, generally "C"-shaped configuration. The distal clip 50 is shown alone in enlarged view in FIGS. 7 and 8.

Figure 7:
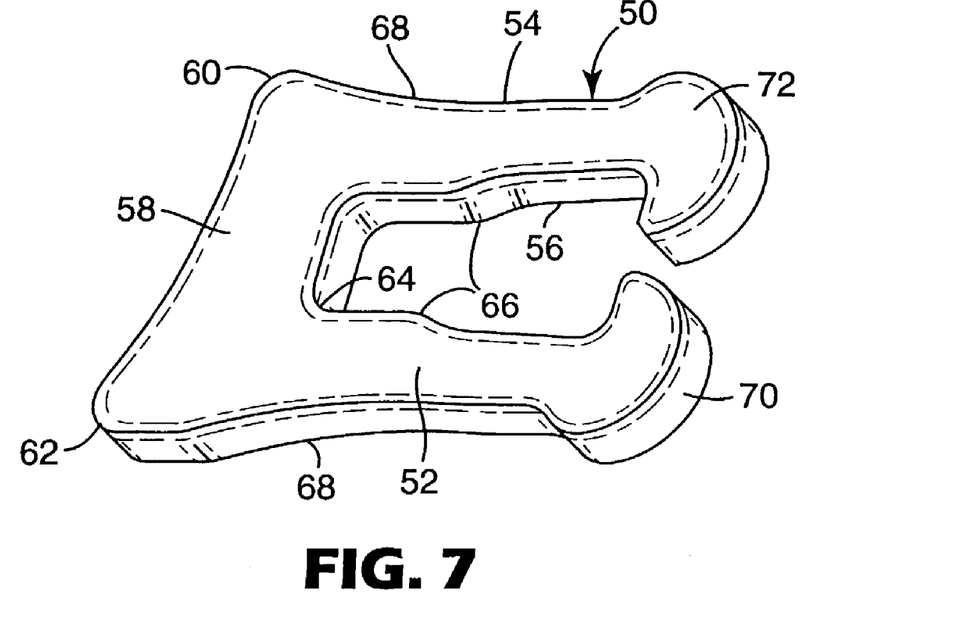
FIG. 7 is an enlarged perspective view of a distal clip that comprises part of a latch of the appliance depicted in FIGS. 1–6.
Figure 8:
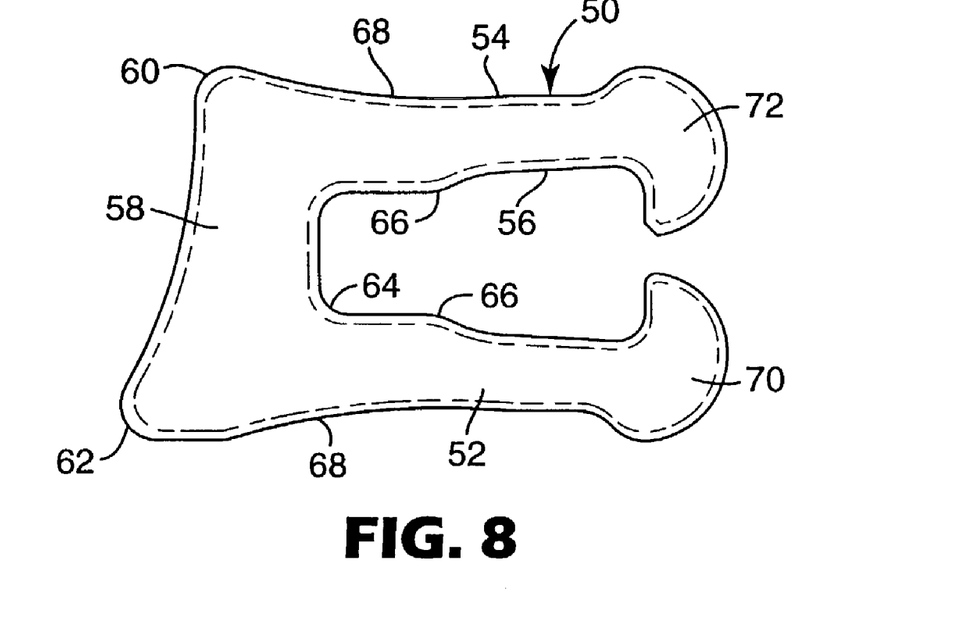
FIG. 8 is a side elevational view of the clip shown in FIG. 7, looking toward a distal side of the clip.

The distal clip 50 includes a first section 52 and a second section 54 that is opposed to the first section 52. In their normal, relaxed configurations, the first section 52 and the second section 54 extend in generally parallel buccolabial directions. The first section 52 is spaced from the second section 54 to present a region 56 for receiving an archwire.

The distal clip 50 also includes a third section 58 that interconnects the first section 52 and the second section 54. When assembled to remaining components of the appliance 20, the third section 58 extends in a generally occlusal-gingival direction along the buccolabial surface of the base 22 as can be appreciated by reference to FIG. 6. The third section 58 extends beyond the first section 52 and the second section 54 in an occlusal-gingival direction and terminates at a rounded, protruding outermost gingival corner 60 and a rounded, protruding outermost occlusal corner 62.

Preferably, and as shown in FIG. 6, the corners 60, 62 contact the buccolabial side of the base 22 when the clip 50 is assembled to remaining components of the appliance 20. However, a middle portion of the third section 58 is slightly spaced from the buccolabial side of the base 22. Such construction ensures that the clip 50 contacts the base 22 at two locations and does not unduly rock about a mesial-distal reference axis during use.

The clip 50 also includes a recess 64 that communicates with the archwire-receiving region 56. The recess 64 is smaller than the region 56 in directions parallel to the direction of extension of the third section 58, which in turn is generally parallel to an occlusal-gingival reference axis. At the entrance to the recess 64, the first and second sections 52, 54 present a pair of opposed protrusions 66 that extend inwardly toward each other. The opposite sides of the first and second sections 52, 54 also present a notch 68 that is opposed to the respective, adjacent protrusion 66.

The clip 50 also has a pair of arm portions 70, 72 that extend inwardly toward each other. A buccolabial edge of the arm portions 70, 72 is smoothly curved in an arc about a mesial-distal reference axis. For the arm portion 72, the smooth outer curve extends in a gingival direction beyond the gingival side of the second section 54. For the arm portion 70, the smooth outer curve extends in an occlusal direction beyond the occlusal side of the first section 52.

The clip 50 is shown in its normal, relaxed orientation in FIGS. 1–8. However, the arm portions 70, 72 are movable away from each other in order to admit or release an archwire into the archwire-receiving region 56 and the archwire slot 34 when desired. To this end, the first and second sections 52, 54 bend in respective arcs away from each other in order to enable the arm portions 70, 72 to move apart from each other.

The smooth, outer curve on the buccolabial side of the arm portions 70, 72 enables the clip 50 to open an admit and archwire into the region 56 by pressing the archwire against the outer curved edges of the arm portions 70, 72. As pressure is exerted on the curved edges by the archwire, the first and second sections 52, 54 deflect away from each other in order to admit the archwire into the region 56. Once the archwire is received in the region 56, the inherent resiliency of the clip 50 and particularly the resiliency of the first and second sections 52, 54 enables the arm portions 70, 72 to spring back toward each other and to their normal, relaxed configuration as shown in the drawings in order to retain the archwire in the archwire slot 34.

Additional aspects of the clip 50 and other alternative constructions are described in applicant's co-pending U.S. patent application Ser. No. 10/287,089, entitled "Orthodontic Appliance with Fatigue-Resistant Archwire Retaining Latch", filed on the same day as the present patent application.

The mesial clip 48 has a somewhat different shape than the distal clip 50 as can be appreciated by comparing FIG. 4 to FIGS. 7 and 8. In particular, the mesial clip 48 is smaller in overall dimensions than the distal clip 50 in directions along a buccolabial-lingual reference axis. In addition, the mesial clip 48 has a recess for receiving the mesial support 38, but the entrance to the recess next to the archwire receiving region is somewhat different in configuration than the entrance to the recess 64 of the clip 50. However, the operation of the clips 48, 50 is essentially the same.

As shown in the drawings, the mesial archwire guide 28 is also smaller in overall dimensions than the distal archwire guide 30 in directions along a buccolabial-lingual reference axis, in corresponding relationship to the difference in overall dimension between the clips 48, 50. Additionally, the bottom or lingual side of the archwire slot 34 is located closer to the base 22 in regions adjacent the mesial flange 42 in comparison to regions adjacent the distal flange 44. Such construction provides what is known as a "distal offset" in order to help prevent unintended rotation of the associated tooth.

To assemble the clip 50 to remaining components of the appliance 20, the clip 50 is preferably put in place before the base 22 is affixed to the body 24. During assembly, the clip 50 is moved in a buccolabial direction in the space between the distal flange 44 and the adjacent distal side of the body 24 and archwire guide 30 while the arm portions 70, 72 are spread apart a distance sufficient to enable the support 40 to be received in the region 56. The clip 50 is then moved further in a buccolabial direction until such time as the support 40 is received in the recess 64.

The clip 48 is preferably installed in a different manner due to the width of the mesial support 38. Specifically, the clip 48 is oriented 90 degrees from the orientation shown in the drawings and moved toward the mesial support 38 in either an occlusal or gingival direction, as appropriate. Once the mesial support is received in the archwire-receiving region of the clip 48, the clip 48 is pivoted 90 degrees and then moved as needed in a buccolabial direction until reaching the position shown in FIGS. 1–6.

Next, the base 22 is affixed to the body 24 by a suitable process such as brazing or welding (for example, laser welding). Once the base 22 is affixed to the body 24, the clips 48, 50 (and particularly the third sections of the clips 48,50) is captured between the supports 38, 40 respectively and the base 22 and are thereafter retained in place. At this time, the region 56 is aligned with the archwire slot 34 as can be appreciated by a comparison of FIGS. 5 and 6. A similar relationship exists with respect to the clip 48.

The clips 48, 50 (including the first and second sections 52, 54) are sufficiently stiff to retain the archwire in the archwire slot during the course of treatment so long as the forces exerted by the archwire on the appliance 20 are below a certain minimum value in a generally buccolabial direction (more particularly, in a direction opposite to the direction of insertion of the archwire in the archwire slot 34). However, whenever the forces exerted by the archwire on the appliance 20 in the same direction are greater than the minimum value, as might occur when unexpectedly high forces are encountered, the first and second sections 52, 54 deflect outwardly and the arm portions 70, 72 move apart from each other to open the clip 50 and enable the archwire to be released from the archwire slot 34. Similar operation occurs in connection with the clip 48. Further details regarding the forces are described in the aforementioned PCT applications entitled "ORTHODONTIC APPLIANCE WITH SELF-RELEASING LATCH", WO01/22901 and US02/09896, both of which are expressly incorporated by reference herein.

The latch 46, comprising the clips 48, 50, preferably releases the archwire from the archwire slot 34 in a generally buccolabial direction whenever the archwire exerts a force in the same direction on the appliance 20 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 34 during the normal course of orthodontic treatment. As such, the archwire can exert forces on the appliance 20 sufficient to carry out the treatment program and move the associated teeth as desired.

Preferably, the minimum value for self-release (i.e., self-opening) of the latch 46 is substantially less than the force required in the same direction to debond the appliance 20 from the associated tooth. The minimum value for self-release of the latch 46 is preferably less than about one-half of the force required in the same direction to debond the appliance 20 from the associated tooth. For example, if the expected bond strength of the adhesive bond between the appliance 20 and the associated tooth is 16 lbs (7.2 kg) in a buccolabial direction, the latch 46 is constructed to self-release the archwire whenever the archwire exerts a force in the same buccolabial direction on the appliance 20 that is somewhat greater than about 8 lbs (3.6 kg).

To determine the force to release the latch 46, a section of archwire is selected having an area in longitudinally transverse sections that is complemental to (i.e., substantially fills) the cross-sectional area of the archwire slot 34. Next, a sling is constructed and is connected to the archwire section at locations closely adjacent, but not in contact with the mesial flange 42 and the distal flange 44. Optionally, the sling is welded or brazed to the archwire section. Next, the sling is pulled away from the appliance 20 while the appliance 20 is held in a stationary position, taking care to ensure that the longitudinal axis of the archwire section does not tip relative to the longitudinal axis of the archwire slot 34. The force to release the latch 46 may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

The self-releasing latch 46 is a benefit to the practitioner, in that the likelihood of spontaneous debonding of the appliance 20 is substantially reduced. For example, if the practitioner attempts to place a relatively large archwire in the archwire slot 34 and the latch 46 self-releases as soon as the practitioner releases the archwire, the practitioner can then use an archwire with less stiffness in its place so that the appliance 20 is not detached from the tooth surface. As another example, if the archwire is initially held in the archwire slot 34 by the arm portions 70, 72 and the archwire subsequently exerts a larger force on the appliance 20 (as may occur, for example, when the archwire encounters a hard object such as when the patient is chewing relatively hard food), the arm portions 70, 72 spread apart to their slot-open positions to release the archwire so that the appliance 20 does not debond from the tooth. Treatment can then be resumed by merely replacing the archwire in the archwire slot 34 without the need to rebond the base 22 to the associated tooth.

Preferably, the distance between the opposed ends of the arm portions 70, 72 is less than the overall occlusal-gingival dimension of the smallest archwire expected to be used during the course of treatment. The archwire need not fill the archwire slot 34 and flatly engage the wall portions defining the archwire slot 34 in all instances. For example, a somewhat smaller wire, and perhaps an archwire having a circular cross-sectional shape, may be used during a portion of the treatment program. The distance between the opposed ends of the arm portions 70, 72 is preferably selected so that a variety of archwires of different cross-sectional configurations may be used in connection with the appliance 20.

An outermost labial surface of the clips 48, 50 is presented along the labial ends of the arm portions 70, 72. Advantageously, these outermost labial surfaces are located lingually of the outermost buccolabial ends of the occlusal arm and the gingival arm of the archwire guides 28, 30 respectively. As such, when an attempt is made to insert an archwire into the region 56 of the clips 48, 50, the occlusal and gingival arms of the archwire guides 28, 30 typically contact the archwire before the archwire engages the arm portions 70, 72 of the clips 48, 50. The occlusal and gingival arms of the archwire guides 28, 30 serve to properly orient the archwire during insertion of the archwire into the region 56 so that proper opening movement of the arm portions 70, 72 of the clips 48, 50 is facilitated.

Optionally, the spring clips 48, 50 are cut from a flat section of metallic stock material. Suitable metallic materials include shape memory alloys such as alloys of nitinol and beta-titanium. The clips 48, 50 may be cut from the stock material using a stamping, die cutting, chemical etching, EDM (electrical discharge machining), laser cutting or water jet cutting process. As another option, the clips 48, 50 could be formed and then heat treated to set their shapes.

As presently preferred, the clips 48, 50 are made from flat annealed superelastic material (such as nitinol) having a pickled surface. Preferred nitinol materials have a nickel content of 55.97% by weight $A_f$ of 10°±5° C. The nitinol is cold worked to 37.5% and has a thickness in the range of about 0.012 in. (0.3 mm) to about 0.016 in. (0.4 mm). The clips 48, 50 are first cut in a rough cutting EDM process, then cut along their edges for an additional one or more times using an EDM process in order to round the edges. Alternatively, a laser cutting process or chemical etching process could be used to make the clips 48, 50. Preferably, the clips 48, 50 are constructed so that the longitudinal direction of the clip material, or the principal direction of grain flow of the clip material, is substantially parallel to a buccolabial-lingual reference axis, or the direction of extension of the first and second sections 52, 54.

Subsequent to the EDM, laser cutting or chemical etching process, the clips 48, 50 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size 3/16×3/8 (4.7 mm×9.5 mm), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. T1121 Pickling Solution from Aya International of Los Angeles, Calif.

Advantageously, the shape of the clip 50 as shown in FIGS. 6–8 reduces maximum strain and stress during opening and closing movements so that the expected useful life of the clip 50 is increased. In particular, the decrease in width of the first and second sections 52, 54 as the arm portions 70,72 are approached serves to reduce maximum strain to significantly lower levels. Preferably, this decrease in width is a dimension that is determined along an occlusal-gingival reference axis and the decrease in width is carried out gradually as the arm portions 70, 72 are approached. The provision of the recess 64 also helps to reduce maximum strain and stress when the clip 50 is opened during assembly of the appliance 20. The provision of the notches 68 helps to safely provide a gradual decrease in width while enabling the recess 64 to be smaller than the region 56 in directions along an occlusal-gingival reference axis. As an example, it was found in one analysis that careful selection of the overall shape of the perimeter of the first and second sections 52, 54 helped to reduce maximum strain from 0.116 to 0.067 and maximum stress from 98,700 psi to 75,200 psi.

Optionally, and as shown in the drawings, the third section 58 extends in a direction other than 90 degrees from the direction of extension of the first and second sections 52, 54 when the clip 50 is in its normally relaxed orientation. Additionally, a hypothetical reference plane resting on an outer edge of the third section 58 extends in a direction other than 90 degrees from the direction of extension of the first and second sections 52, 54 when the clip 50 is in its normally relaxed configuration. Such construction is particularly useful for appliances having what is known as "torque-in-base" such as the molar appliance 20 as shown in FIGS. 1–6.

For example, and with reference to FIG. 6, the torque-in-base appliance has an archwire slot with a lingual wall that is oriented at an acute angle relative to the overall orientation of the base 22. The orientation of the third section 58 helps ensure that the corners 60, 62 firmly bear against the buccolabial side of the base 22 once the clip 50 is assembled to remaining components of the appliance 20. For brackets with a zero degree torque, the reference plane mentioned above extends at a substantially 90 degree direction from the direction of the first and second sections 52, 54, but in those instances it is also preferred that the corners 60, 62 firmly bear against the buccolabial side of the base 22.

The assembly of the body 24, guides 28, 30, hook 36, flanges 42, 44 and supports 38, 40 is preferably an integral unitary structure and may be made by any suitable manufacturing process such as machining or injection molding (including metal injection molding). This assembly may be made of stainless steel such as no. 17-4 PH, although other materials are also possible. Preferably, the tumbling and heat treating operations are carried out after the assembly is fabricated.

The channel 32 is an advantage in that it provides a convenient location for the practitioner to grip the appliance 20 during placement of the same on the patient's tooth surface. For example, the practitioner may elect to place one tip of fine-tipped pliers into the channel 32 and the other tip along the mesial side of the appliance 20. Holding the appliance 20 in this manner provides a more secure connection as compared, for example, to grasping the appliance with a pair of pliers across its mesial and distal sides.

Additionally, the channel 32 provides a location for placement of a stop along the length of the archwire in order to help avoid unintentional movement of the archwire in a mesial or distal direction. For example, the practitioner may elect to form a small bend in the shape of a "V" in the archwire to make, in effect, a lateral protrusion for the archwire. This bend is then placed in the channel 32 in order to resist undue movement of the archwire in a mesial or distal direction along the archwire slot 34. Alternatively, a 90 degree bend can be placed in the archwire such that the outermost, bent end of the archwire extends outwardly in a lateral direction from the archwire slot 34 and through the channel 32. Bends such as these can help prevent extended movement of the ends of the archwire past the distal side of the appliance 20 so that undesired contact of the archwire with the patient's adjacent soft tissue can be avoided.

Furthermore, the channel 32 provides a passage for receiving a hand instrument useful for releasing the archwire from the archwire slot 34. For example, a hand instrument in the nature of a prying tool may be inserted in the channel 32 between the lingual side of the archwire and the buccolabial side of the base 22. By proper manipulation of the hand instrument, pressure can be exerted on the archwire in a buccolabial direction in order to shift the clips 48, 50 to an open orientation and thereby release the archwire from the archwire slot 34.

As shown for example in FIG. 1, the lingual side of the channel 32 is located in a lingual direction relative to the bottom or lingual side of the archwire slot 34. Additionally, the archwire slot 34 lacks occlusal and gingival sides in the area of the channel 32. Such construction reduces the amount of surface area of the appliance 20 in engagement with the archwire in comparison to molar appliances having a continuous passageway or archwire slot along substantially their entire length. Moreover, this open-type construction reduces the likelihood that an undue amount of plaque will accumulate in the archwire slot 34.

As shown in FIGS. 1 and 5, the distal flange 44 of the appliance 20 has at least one groove, and preferably has two grooves 74 that are located directly adjacent the base 22. One of the grooves 74 is located along an occlusal side of the appliance 20 while the remaining groove 74 is located along the gingival side of the appliance 20. Each of the grooves 74 presents an overhanging shoulder that serves to retain a wire segment or other item in place.

Preferably, each groove 74 has a height in a labial-lingual direction that is sufficient for holding an elongated wire segment in place. Preferably, the overall labial-lingual height of the groove 74 is at least 0.005 in. (0.13 mm) and more preferably is at least 0.008 in. (0.2 mm). Preferably, each groove 74 also has an overall width in an occlusal-gingival direction that is at least 0.005 in. (0.13 mm) and more preferably is at least 0.008 in. (0.2 mm).

The grooves 74 are particularly useful for retaining a tieback loop in place. For example, an orthodontic practitioner who has a patient with a gap between two adjacent teeth, such as a bicuspid tooth and the adjacent cuspid tooth, may desire to use a tieback loop for closing the space over a period of time. To make the tieback loop, a wire segment is used to interconnect the bracket that is mounted on the patient's bicuspid tooth and the bracket that is mounted on the patient's cuspid tooth as well as the molar appliance 20 so that a force can be directed on the cuspid tooth to eventually close the space. The wire segment is formed and tied in a loop (called a "tieback loop") about the brackets and/or the appliances. An example of a suitable wire segment is a stainless steel wire segment having a diameter in the range of about 0.010 in. (0.25 mm) to about 0.014 in. (0.35 mm).

As one specific example of a tieback loop, the wire segment is installed along a path that extends along the gingival and occlusal sides of the appliance 20 as well as the occlusal and gingival sides of the cuspid and bicuspid brackets mentioned above. This wire segment is also received in the grooves 74 as well as along the distal side of the distal flange 44 in a location adjacent the base 22.

The grooves 74 as described above can also be advantageously used to retain items other than tieback loops. For example, the grooves 74 may be used to hold in captive relationship a wire segment that ties a number of teeth together, as may be desired to serve as anchorage for one or more other orthodontic appliances. The grooves 74 may also serve to retain certain elongated members in place along the sides of the appliances that are connected to other teeth, or serve as a point of connection to other devices that are used during the course of orthodontic treatment.

The appliance 20 shown in the drawings is adapted for a patient's upper right first molar tooth. However, the various features of the appliance 20 may be adapted for use in appliances constructed for other teeth as well. For example, an appliance for a lower right or left first molar tooth may be substantially similar to the appliance 20 shown in the drawings, except that preferably the mesial and distal archwire guide have a similar length in directions along a buccolabial-lingual reference axis and no distal offset is provided.

Figure 9:
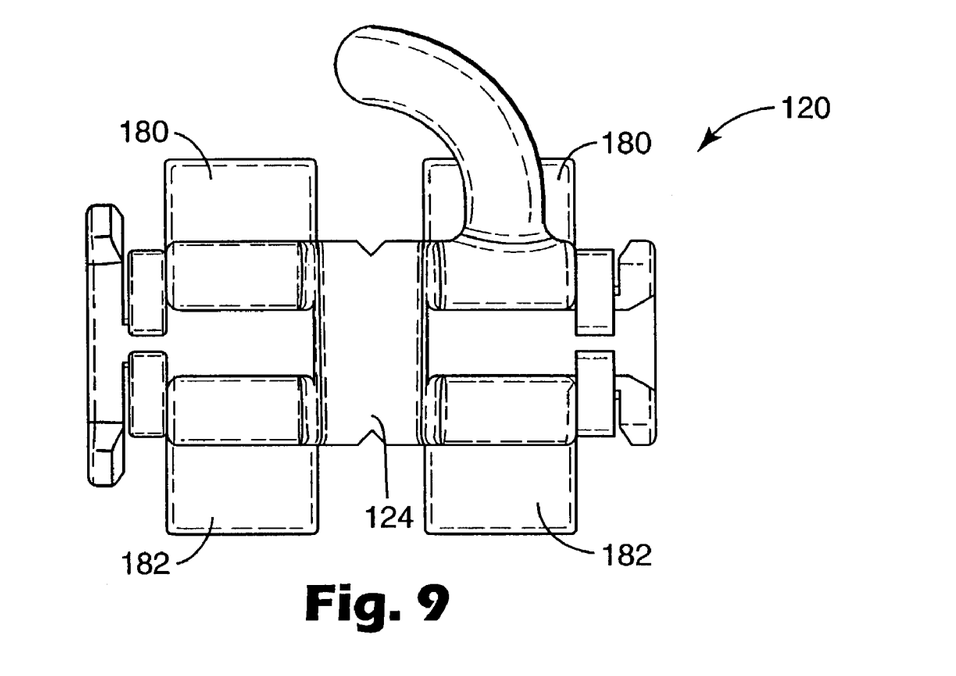
FIG. 9 is a front elevational view of an orthodontic appliance for a molar tooth according to another embodiment of the invention, looking at the appliance toward its buccolabial side.
Figure 10:
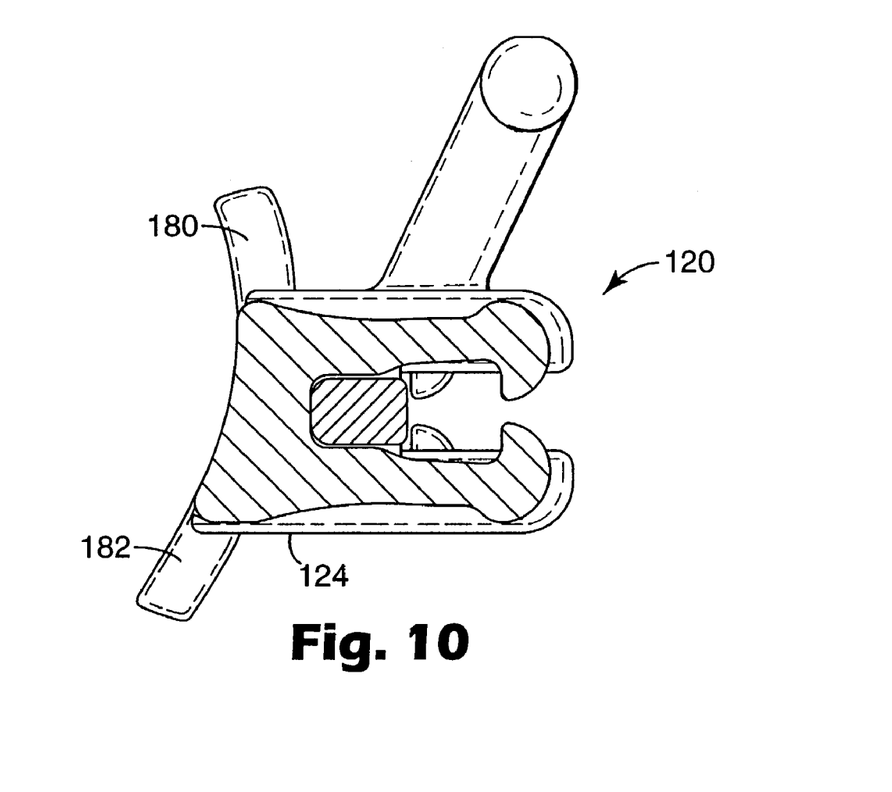
FIG. 10 is an enlarged end cross-sectional view of the appliance illustrated in FIG. 9 and looking in a direction toward the distal side of the appliance.

A molar appliance 120 according to other embodiment of the invention is shown in FIGS. 9 and 10. The appliance includes a body 124 but lacks a base that is suitable for direct bonding to a tooth surface. Instead, the appliance 120 has a base that includes two occlusal flanges 180 and two distal flanges 182. The flanges 180, 182 are adapted to be affixed to an orthodontic band by a welding or brazing process. Preferably, the flanges 180, 182 are integrally connected to the body 124.h Other aspects of the appliance 120 are similar to the various aspects of the appliance 20. Accordingly, a detailed description of the features in common need not be repeated.

Those skilled in the art may recognize that a number of variations and additions may be made to the various embodiments described above without departing from the spirit of the invention. Accordingly, this invention should not be deemed limited to the specific embodiments set out in detail, but instead only by a fair scope of the claims that follow along with their equivalents.

What is claimed is:

1. An orthodontic appliance for a molar tooth comprising:
   a base for connecting the appliance to a molar tooth;
   a body extending from the base, the body having a mesial side portion and a distal side portion;
   a mesial archwire guide connected to the mesial side portion of the body;
   a distal archwire guide connected to the distal side portion of the body;
   an archwire slot extending across the mesial archwire guide and the distal archwire guide in generally mesial-distal direction; and
   a latch for releasably retaining an archwire in the archwire slot, the latch being movable from a slot-open position for admitting the archwire in the archwire slot to a slot-closed position for retaining the archwire in the archwire slot, wherein the latch comprises a mesial clip located mesially of the mesial archwire guide and a distal clip located distally of the distal archwire guide, wherein the appliance lacks tiewings, wherein the distal archwire guide is spaced from the mesial archwire guide to present a channel that extends in a general occlusal-gingival direction, wherein the mesial clip is smaller in overall dimensions than the distal clip in directions along a buccolabial-lingual reference axis, and wherein the mesial archwire guide is smaller in overall dimensions than the distal archwire guide in directions along buccolabial-lingual reference axis.

2. An orthodontic appliance for a molar tooth according to claim 1 wherein the mesial archwire guide and the distal archwire guide have outermost labial ends, and wherein the mesial clip and the distal clip have outermost labial surfaces that are located lingually of the labial ends of the mesial archwire guide and the distal archwire guide respectively.

3. An orthodontic appliance for a molar tooth according to claim 1 wherein the appliance includes a mesial support extending in a mesial direction outwardly from the mesial archwire guide, and wherein the mesial clip is coupled to the mesial support.

4. An orthodontic appliance for a molar tooth according to claim 1 wherein the latch self-releases the archwire from the archwire slot whenever the archwire exerts a force on the latch that exceeds a certain value.

5. An orthodontic appliance for a molar tooth according to claim 1 wherein the mesial archwire guide and the distal archwire guide each have an occlusal arm and a gingival arm that extend in generally parallel directions relative to each other.

6. An orthodontic appliance for a molar tooth according to claim 5 wherein the occlusal arm and the gingival arm of the mesial archwire guide and the distal archwire guide have curved outermost labial ends.

7. An orthodontic appliance for a molar tooth according to claim 1 wherein the channel and the archwire slot each have a lingual side, and wherein the lingual side of the channel is spaced in a lingual direction from the lingual side of the archwire slot.

8. An orthodontic appliance for a molar tooth according to claim 1 wherein the appliance includes a mesial support extending in a mesial direction from the mesial archwire guide, and wherein the appliance includes a distal support extending in a distal direction from the distal archwire guide, and wherein the latch comprises a mesial clip that extends about the mesial support and a distal clip that extends about the distal support.

9. An orthodontic appliance for a molar tooth according to claim 8 wherein the mesial support has a labial side, and wherein the archwire slot has a lingual side next to the mesial archwire guide that is generally co-planar with the labial side of the mesial support.

10. An orthodontic appliance for a molar tooth according to claim 8 wherein the appliance includes a mesial flange connected to the mesial support and a distal flange connected to the distal support, and wherein the mesial flange is located in a mesial direction relative to the mesial clip and wherein the distal flange is located in a distal direction relative to the distal clip.

11. An orthodontic appliance for a molar tooth according to claim 10 wherein at least one flange has at least one groove adjacent the base of the appliance for retaining a wire segment or other item in place.

12. An orthodontic appliance for a molar tooth according to claim 8 wherein the distal clip includes an archwire-receiving region and a recess adjacent the archwire-receiving region, wherein the distal support is received in the recess.

13. An orthodontic appliance for a molar tooth according to claim 12 wherein the recess is smaller than the region in directions generally parallel to an occlusal-gingival reference axis.

14. An orthodontic appliance for a molar tooth according to claim 1 wherein the base is adapted for direct bonding to a surface of a tooth.

15. An orthodontic appliance for a molar tooth according to claim 1 wherein the base includes at least one flange for coupling the appliance to a band.

* * * * *

UNITED STATES PATENT AND TRADEMARK OFFICE
CERTIFICATE OF CORRECTION

PATENT NO. : 6,957,957 B2
DATED : October 25, 2005
INVENTOR(S) : Pospisil, Jirina V.

It is certified that error appears in the above-identified patent and that said Letters Patent is hereby corrected as shown below:

Column 13,
Line 27, after "in" insert -- a --.
Line 31, after "slot" insert -- and --.
Line 38, delete "general" and insert -- generally --.
Line 44, after "along" insert -- a --.

Signed and Sealed this

Twenty-fourth Day of January, 2006

JON W. DUDAS
*Director of the United States Patent and Trademark Office*